(12) United States Patent
Cui et al.

(10) Patent No.: US 12,049,412 B2
(45) Date of Patent: Jul. 30, 2024

(54) VERMICOMPOST MADE OF AQUATIC PLANTS AND PREPARATION METHOD AND USE THEREOF

(71) Applicant: INSTITUTE OF BOTANY JIANGSU PROVINCE AND CAS, Nanjing (CN)

(72) Inventors: Jian Cui, Nanjing (CN); Jinfeng Li, Nanjing (CN); Dongrui Yao, Nanjing (CN); Jianwei Cui, Nanjing (CN); Wei Wang, Nanjing (CN); Yajun Chang, Nanjing (CN); Xiaojing Liu, Nanjing (CN)

(73) Assignee: INSTITUTE OF BOTANY JIANGSU PROVINCE AND CAS, Nanjing (CN)

( * ) Notice: Subject to any disclaimer, the term of this patent is extended or adjusted under 35 U.S.C. 154(b) by 31 days.

(21) Appl. No.: 17/878,573

(22) Filed: Aug. 1, 2022

(65) Prior Publication Data

US 2023/0192511 A1  Jun. 22, 2023

(30) Foreign Application Priority Data

Dec. 21, 2021 (CN) .......................... 202111568611.2

(51) Int. Cl.
| | |
|---|---|
| C02F 1/38 | (2023.01) |
| A01C 3/00 | (2006.01) |
| B01J 20/24 | (2006.01) |
| B01J 20/30 | (2006.01) |
| C02F 1/28 | (2023.01) |
| C02F 1/68 | (2023.01) |
| A61K 36/31 | (2006.01) |
| A61K 36/62 | (2006.01) |
| C02F 101/20 | (2006.01) |

(Continued)

(52) U.S. Cl.
CPC ............... *C02F 1/286* (2013.01); *A01C 3/00* (2013.01); *B01J 20/24* (2013.01); *B01J 20/30* (2013.01); *C02F 1/68* (2013.01); *A61K 36/31* (2013.01); *A61K 36/62* (2013.01); *C02F 2101/20* (2013.01); *C05F 3/00* (2013.01)

(58) Field of Classification Search
None
See application file for complete search history.

(56) References Cited

FOREIGN PATENT DOCUMENTS

CN 109160829 A * 1/2019 ................ C05F 3/06

OTHER PUBLICATIONS

Ramos et al. (Bioresource Technology, 2022, 345, 126572), available online Dec. 15, 2021. (Year: 2021).*

(Continued)

*Primary Examiner* — Clare M Perrin
(74) *Attorney, Agent, or Firm* — Resolute Legal PLLC

(57) ABSTRACT

The present disclosure provides vermicompost made of aquatic plants and a preparation method of the vermicompost. The preparation method includes: mixing aquatic plant residues and fresh cow dung according to a proportion, and crushing the aquatic plant residues while stirring until even mixing; adding earthworms to a mixture of the aquatic plant residues and the cow dung, where the earthworms transform the mixture of the aquatic plant residues and the cow dung in a forest at 15-35° C., and moisture in the mixture is maintained at 65-75% in the process; and after 35-45 days, separating the earthworms and vermicompost, and drying the vermicompost to obtain the vermicompost made of aquatic plants.

17 Claims, 6 Drawing Sheets

(51) Int. Cl.
*C02F 103/00* (2006.01)
*C05F 3/00* (2006.01)

(56) References Cited

OTHER PUBLICATIONS

Varma et al. (Ecological Engineering, 2016, 94, 127-135). (Year: 2016).*
Yadav et al. (International Journal of Recycling of Organic Waste in Agriculture, 2013, 2:21, pp. 1-7) . (Year: 2013).*
Asif et al. (Int. J. Curr. Microbio. App. Sci, 2019, 8(1), 1290-1296). (Year: 2019).*
Sharma et al. (Environ. Eng. Res., 2017, 22(3), 237-244). (Year: 2017).*
Machine translation of CN 109160829 A, pp. 1-24. (Year: 2019).*

\* cited by examiner

VERMICOMPOST MADE OF AQUATIC PLANTS AND PREPARATION METHOD AND USE THEREOF

CROSS REFERENCE TO RELATED APPLICATION

This patent application claims the benefit and priority of Chinese Patent Application No. 202111568611.2, filed on Dec. 21, 2021, the disclosure of which is incorporated by reference herein in its entirety as part of the present application.

TECHNICAL FIELD

The present disclosure relates to vermicompost made of aquatic plants and a preparation method and use of the vermicompost, and belongs to the technical field of water purification and restoration.

BACKGROUND ART

Aquatic plants are an important part of water ecosystem, and can effectively absorb nitrogen, phosphorus and heavy metals in the water body and release allelochemicals through absorption, filtration, and interception during growth, which plays a core role in ecological governance of water eutrophication and heavy metal pollution. However, at present, most engineering applications of the aquatic plants generally lack effective management of aquatic plants, and a large number of aquatic plants have not been harvested in time, resulting in the re-release of residual nutrients and heavy metals into the water body, which causes secondary pollution. In addition, the aquatic plants for engineering have low economic value. Even if they are harvested, the storage, transportation, and disposal of a large number of residues are also problems faced by the current society, which affects the improvement of the ecological environment and service functions of the water body and even the basin and the construction process of Beautiful China. With the development of ecological cycle and environment-friendly society, the use of earthworms to dispose plant residues has become one of the ways to realize the recycling of plant residues and harvest of earthworms, which has both environmental and economic benefits and is widely concerned and promoted.

Water resources are basic natural resources and strategic economic resources that are related to the national economy and the people's livelihood. With the rapid development of industry and agriculture and the increase of population, as well as the discharge of "three wastes" (waste gas, waste water, and waste residues) related to the heavy metal industry and the extensive use of its products, the heavy metal industry has become an important factor threatening the global water environment security and human health, and has been widely concerned by all walks of life. In recent years, heavy metal pollution incidents have occurred frequently in China. The pollution of typical heavy metals such as copper and zinc in the water body is on the rise, and the compound pollution situation is severe. At present, the methods for removing heavy metals from the water body mainly include precipitation, flocculation, redox, ion exchange, membrane separation, phytoremediation, and adsorption. The precipitants, flocculants, adsorbents, resins, and membranes involved in these methods are mostly chemical synthetics or minerals. Their functional properties are relatively single or some of them are costly to use, and most of them are non-renewable resources.

SUMMARY

A technical problem to be solved by the present disclosure is to overcome the defects of the prior art, and provide vermicompost made of aquatic plants and a preparation method and use of the vermicompost. The vermicompost made of aquatic plants adsorbs copper and zinc in a water body through different action mechanisms, so as to remove copper-zinc compound pollution from the water body, find an ecological cycle way for disposal of aquatic plants, especially plant residues used in water ecological restoration projects, and provide an ecological governance method for remediation of combined heavy metal pollution in water.

To solve the above technical problem, the present disclosure provides a preparation method of vermicompost made of aquatic plants, including:

mixing aquatic plant residues and fresh cow dung according to a proportion, and crushing the aquatic plant residues while stirring until even mixing;

adding earthworms to a mixture of the aquatic plant residues and the cow dung, where the earthworms transform the mixture of the aquatic plant residues and the cow dung in a forest at 15-35° C., and moisture in the mixture is maintained at 65-75% in the process; and after 35-45 days, separating the earthworms and vermicompost, and drying the vermicompost to obtain the vermicompost made of aquatic plants.

Further, the mixture of the aquatic plant residues and the cow dung and the earthworms may have a weight ratio of 20:1.

Further, the vermicompost may have a moisture content less than or equal to 30%.

Further, the aquatic plant residues may be fresh lotus leaves or fresh cress.

Further, the aquatic plant residues may be stirred and crushed with a shovel or forklift.

Further, the earthworm may be *Eisenia foetida*.

The present disclosure further provides vermicompost made of aquatic plants prepared by the above preparation method.

The present disclosure further provides use of the above vermicompost made of aquatic plants in removing copper-zinc compound pollution from a water body.

Further, the vermicompost made of aquatic plants may have a dosage of 1.0-2.0 g $L^{-1}$.

The transformation products of earthworms, such as organic wastes including aquatic plant residues, have complex and diverse physical and chemical properties, have various capture mechanisms for heavy metal ions: physical adsorption, complexation reaction, ion exchange, and chemical precipitation, have the characteristics of most adsorbents, and are mostly renewable resources.

There are significant differences in the binding forms of copper and zinc in the vermicompost made of aquatic plants (FIG. 6). The adsorbed copper is mainly in an acid-soluble state and a residual state, accounting for 20.47% and 74.89% respectively. The adsorbed zinc is mainly in an ion-exchange state, an acid-soluble state and a residual state, accounting for 26.65%, 55.56%, and 16.55% respectively.

The beneficial effects of the present disclosure are:

The materials used in the present disclosure are aquatic plant (fresh lotus leaves and fresh cress) residues and fresh cow dung, which are transformed by the earthworms at certain moisture and temperature, and after harvesting, the quality of the earthworms is improved. The vermicompost made of aquatic plants adsorbs copper and zinc in the water body through different action mechanisms, so as to remove copper-zinc compound pollution from the water body. The removal rates of copper and zinc from the water body reaches 93.84-94.27% and 96.85-96.95% respectively, which are 9.11-9.82% and 6.77-6.87% higher than that of conventional vermicompost (with only cow dung as the raw material) (FIG. 1).

DETAILED DESCRIPTION OF THE EMBODIMENTS

Figure 1:
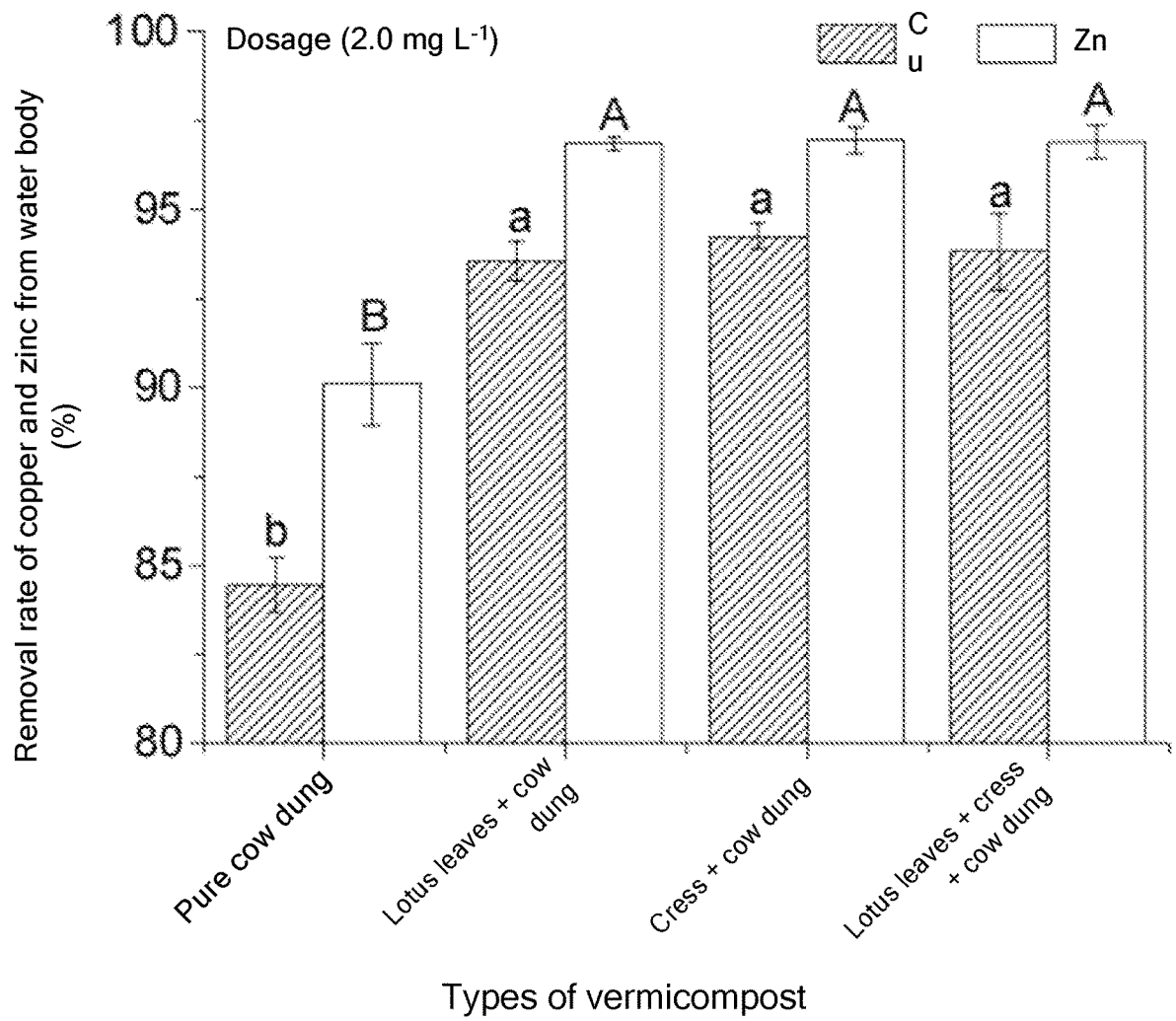
FIG. 1 shows removal effects of vermicompost made of aquatic plants on copper and zinc in a compound polluted water body.

The present disclosure is further described below with reference to examples. The following examples are only used for describing the technical solutions of the present disclosure more clearly, and are not intended to limit the protection scope of the present disclosure.

Based on the enterprise standards for wastewater discharge involving heavy metals, $CuSO_4$ and $ZnCl_2$ are used to prepare a copper-zinc compound polluted water body, and copper and zinc have concentrations of 2.0 and 8.0 mg $L^{-1}$ respectively.

EXAMPLE 1

Preparation of Lotus Leaf Vermicompost and its Removal Effect on Copper-Zinc Compound Pollution in a Water Body A preparation method of lotus leaf vermicompost included the following steps.

(1) Fresh lotus leaves and fresh cow dung were mixed according to a proportion. The fresh lotus leaves and the cow dung were each 50% by weight. The lotus leaves were crushed with a shovel or forklift while stirring until even mixing.

(2) *Eisenia foetida* was added to a mixture of the fresh lotus leaves and the cow dung. The mixture of the fresh lotus leaves and the cow dung and the earthworms had a weight ratio of 20:1. The earthworms transformed the mixture of the fresh lotus leaves and the cow dung in a forest at 15° C., and moisture in the mixture was maintained at 65% in the process.

(3) After 45 days, the earthworms and vermicompost were separated, and vermicompost was dried to obtain the lotus leaf vermicompost.

The crude ash content of the earthworms was significantly reduced, from 24.24% of earthworms produced from pure cow dung to 13.07% (FIG. 2), reaching the level I of fishmeal (GB/T 19164-2003). The vermicompost had a pH of 9.08-9.12, which was 8.63% lower than that of vermicompost produced from pure cow dung on average. The dosages of the vermicompost were set as 0, 1.0, 2.0, 4.0, 5.0, 10.0, 15.0, 20.0, 25.0 and 30.0 g $L^{-1}$. The vermicompost was shaken in a constant temperature shaker at 25° C. for 24 h and centrifuged, and concentrations of the copper and zinc in supernatant were tested. The results showed that the removal rates of copper and zinc from the water body by the vermicompost produced from pure cow dung were 70.93-86.14% and 90.06-96.17%, respectively, and with the increase of the dosage, the removal rate of copper decreased while that of zinc increased (FIG. 3). The addition of vermicompost produced from lotus leaves significantly improved the removal effect of copper and zinc from the water body, and the maximum removal rates reached 93.88% and 98.22% respectively. The optimum dosage of the lotus leaf vermicompost was 2 g $L^{-1}$. At this time, copper and zinc in equilibrium liquid had concentrations of 0.13 and 0.25 mg $L^{-1}$ respectively (FIG. 4), reaching the level II of surface water (GB 3838-2002).

EXAMPLE 2

Preparation of Cress Vermicompost and its Removal Effect on Copper-Zinc Compound Pollution in a Water Body A preparation method of cress vermicompost included the following steps.

(1) Fresh cress and fresh cow dung were mixed according to a proportion. The fresh cress and the cow dung were each 50% by weight. The cress was crushed with a shovel or forklift while stirring until even mixing.

(2) *Eisenia foetida* was added to a mixture of the fresh cress and the cow dung. The mixture of the fresh cress and the cow dung and the earthworms had a weight ratio of 20:1. The earthworms transformed the mixture of the fresh cress and the cow dung in a forest at 35° C., and moisture in the mixture was maintained at 75% in the process.

(3) After 35 days, the earthworms and vermicompost were separated, and the vermicompost was dried to obtain the cress vermicompost.

Figure 2:
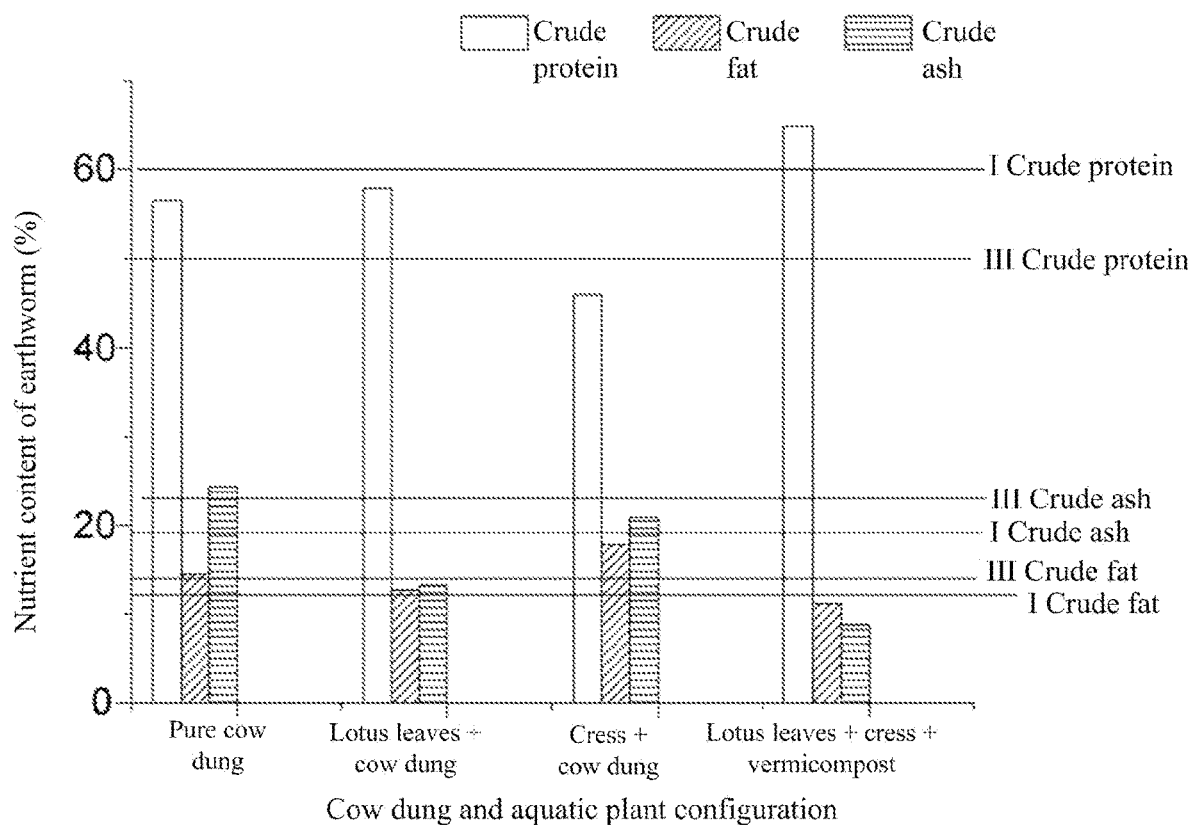
FIG. 2 shows effects of added aquatic plants on quality of earthworms.
Figure 3:
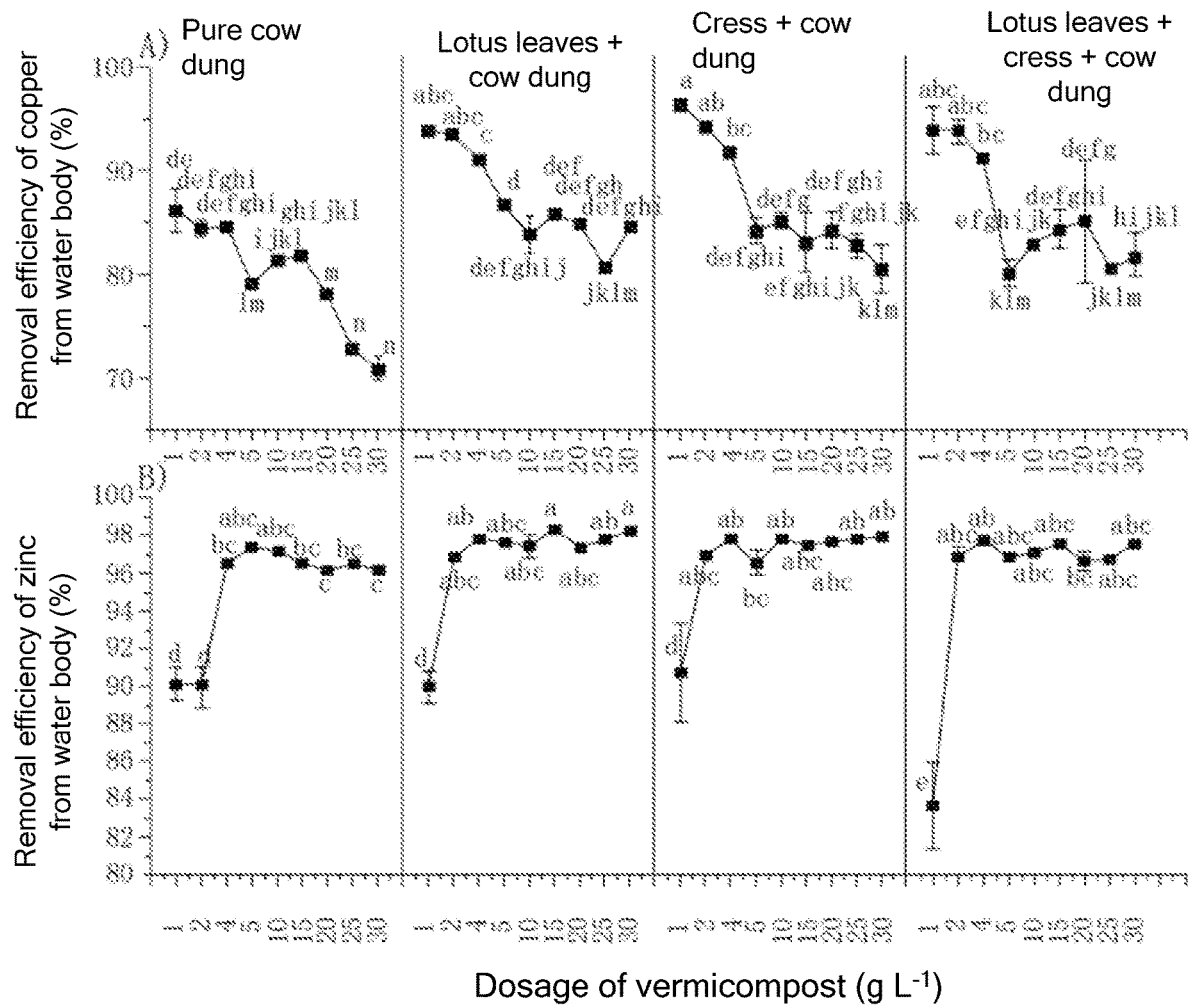
FIG. 3 shows removal effects of dosages of the vermicompost made of aquatic plants on the copper (A) and the zinc (B) in the compound polluted water body.
Figure 4:
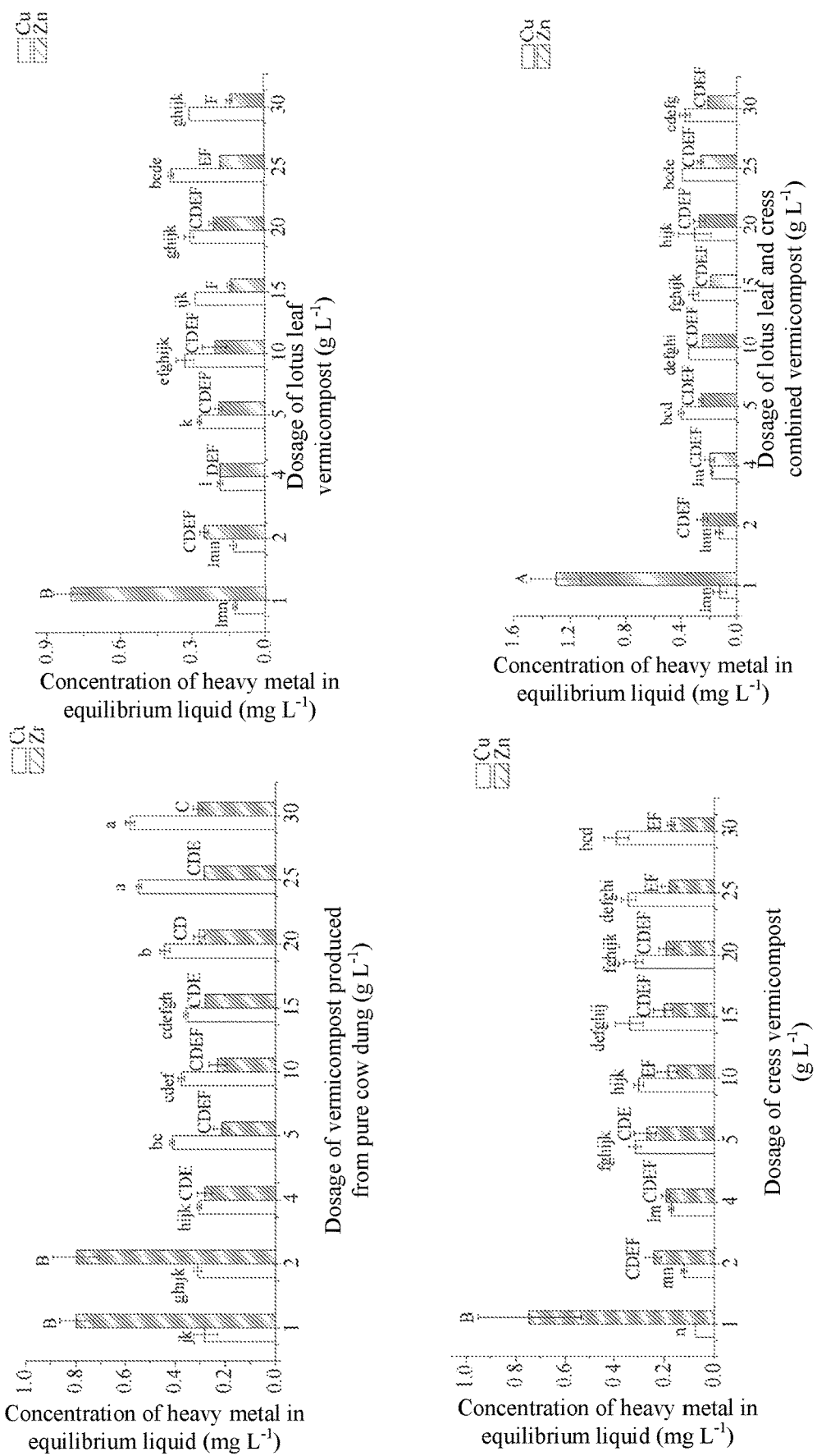
FIG. 4 shows effects of dosages of different vermicompost made of aquatic plants on concentrations of the copper (A) and the zinc (B) in the compound polluted water body.

Compared with earthworms produced from pure cow dung, the quality of earthworms produced by adding cress decreased slightly (FIG. 2). The vermicompost had a pH of 9.90-9.92, which was equivalent to that of vermicompost produced from pure cow dung. The dosages of the vermicompost were set as 1.0, 2.0, 4.0, 5.0, 10.0, 15.0, 20.0, 25.0 and 30.0 g $L^{-1}$. The vermicompost was shaken in a constant temperature shaker at 25° C. for 24 h and centrifuged, and concentrations of the copper and zinc in supernatant were tested. The results showed that compared with the vermicompost produced from pure cow dung, the vermicompost produced by adding cress improved the overall removal effects of copper and zinc from the water body (FIG. 3). With the increase of the dosage of the cress vermicompost, the removal efficiency of copper from the water body showed a downward trend, and the larger removal rates (93.56% and 93.87%) were reached when the dosages were 1.0 and 2.0 g $L^{-1}$. The removal rate of zinc from the water body increased with its dosage, but there was no significant difference (p>0.05) in the removal efficiency of zinc from the water body among the last 8 dosages, which was significantly higher than that of 1.0 g $L^{-1}$. It can be seen that the optimum dosage of the cress vermicompost was 2.0 g $L^{-1}$. At this time, copper and zinc in equilibrium liquid had concentrations of 0.12 and 0.24 mg $L^{-1}$ respectively (FIG. 4), reaching the level II of surface water (GB 3838-2002).

EXAMPLE 3

Lotus Leaf and Cress Combined Vermicompost and its Removal Effect on Copper-Zinc Compound Pollution in a Water Body A preparation method of lotus leaf and cress combined vermicompost included the following steps.

(1) Fresh lotus leaves, cress, and fresh cow dung were mixed according to a proportion. The fresh lotus leaves, the cress, and the cow dung were 25%, 25%, and 50% by weight. The lotus leaves and the cress were crushed with a shovel or forklift while stirring until even mixing.

(2) *Eisenia foetida* was added to a mixture of the fresh lotus leaves, the cress, and the cow dung. The mixture of the fresh lotus leaves, the cress, and the cow dung and the earthworms had a weight ratio of 20:1. The earthworms transformed the mixture of the fresh lotus leaves, the cress, and the cow dung in a forest at 25° C., and moisture in the mixture was maintained at 70% in the process.

(3) After 40 days, the earthworms and vermicompost were separated, and the vermicompost was dried to obtain the lotus leaf and cress combined vermicompost.

Compared with earthworms produced from pure cow dung, the quality of earthworms produced by adding a combination of cress and lotus leaves was significantly improved (FIG. 2). The increase rate of crude protein was 14.93%, while the decrease rates of crude fat and crude ash were 22.43% and 63.61% respectively, reaching the level I of fishmeal (GB/T 19164-2003). The lotus leaf and cress combined vermicompost had a pH of 10.02-10.06, which was equivalent to that of vermicompost produced from pure cow dung. The dosages of the lotus leaf and cress combined vermicompost were set as 0, 1.0, 2.0, 4.0, 5.0, 10.0, 15.0, 20.0, 25.0 and 30.0 g $L^{-1}$. The vermicompost was shaken in a constant temperature shaker at 25° C. for 24 h and centrifuged, and concentrations of the copper and zinc in supernatant were tested. The results showed that compared with the vermicompost produced from pure cow dung, the vermicompost produced by adding a combination of cress and lotus leaves improved the overall removal effects of copper and zinc from the water body (FIG. 3). With the increase of the dosage of the lotus leaf and cress combined vermicompost, the removal efficiency of copper from the water body showed a downward trend, and the larger removal rates (93.83% and 93.84%) were reached when the dosages were 1.0 and 2.0 g $L^{-1}$. The removal rate of zinc from the water body is relatively stable and not affected by its dosage (except 1.0 g $L^{-1}$). It can be seen that the optimum dosage of the lotus leaf and cress combined vermicompost was 2.0 g $L^{-1}$. At this time, copper and zinc in equilibrium liquid had concentrations of 0.13 and 0.25 mg $L^{-1}$ respectively (FIG. 4), reaching the level II of surface water (GB 3838-2002).

EXAMPLE 4

Removal Effect and Mechanism of Cress Vermicompost on Copper, Zinc, and Copper-Zinc Compound Pollution A preparation method of cress vermicompost included the following steps.

(1) Fresh cress and fresh cow dung were mixed according to a proportion. The fresh cress and the cow dung were each 50% by weight. The cress was crushed with a shovel or forklift while stirring until even mixing.

(2) *Eisenia foetida* was added to a mixture of the fresh cress and the cow dung. The mixture of the fresh cress and the cow dung and the earthworms had a weight ratio of 20:1. The earthworms transformed the mixture of the fresh cress and the cow dung in a forest at 35° C., and moisture in the mixture was maintained at 75% in the process.

(3) After 35 days, the earthworms and vermicompost were separated, and the vermicompost was dried to obtain the cress vermicompost.

Figure 5:
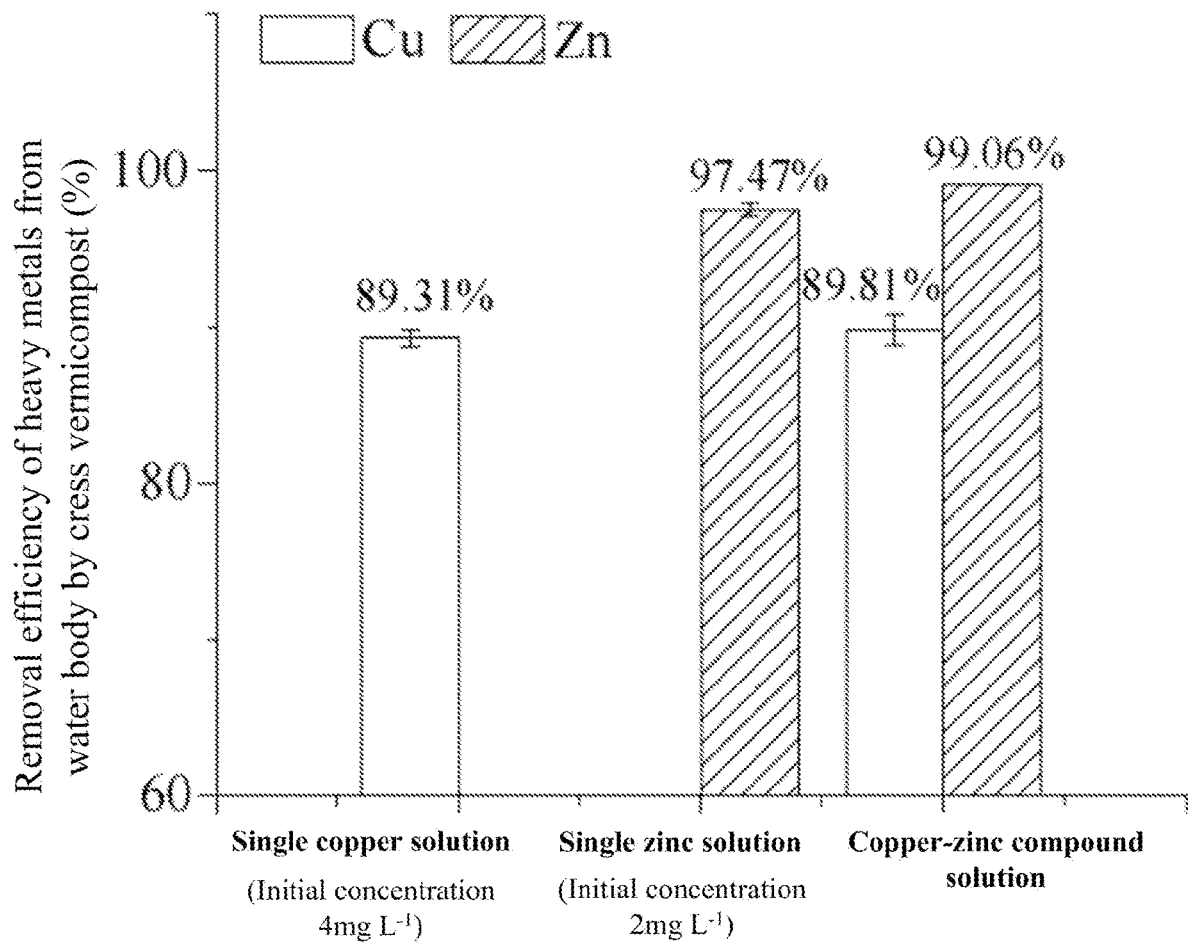
FIG. 5 shows removal effects of cress vermicompost on copper and zinc in their single and compound polluted water bodies.

2.0 g of cress vermicompost were put into three heavy metal solutions: a single copper solution (4.0 mg $L^{-1}$), a single zinc solution (2.0 mg $L^{-1}$), and a copper-zinc compound polluted solution (4.0 mg Cu $L^{-1}$ and 2.0 mg Zn $L^{-1}$). After 24 hours of action, the removal rates of copper and zinc by the cress vermicompost were 89.31-89.81% and 97.47-99.06% respectively (FIG. 5). Compared with single copper and zinc pollution, the removal effect of the cress vermicompost on copper and zinc in the copper-zinc compound polluted solution was not reduced, but improved slightly. It can be seen that the effect of the cress vermicompost on copper and zinc (including compound pollution) in the water body was obvious.

Figure 6:
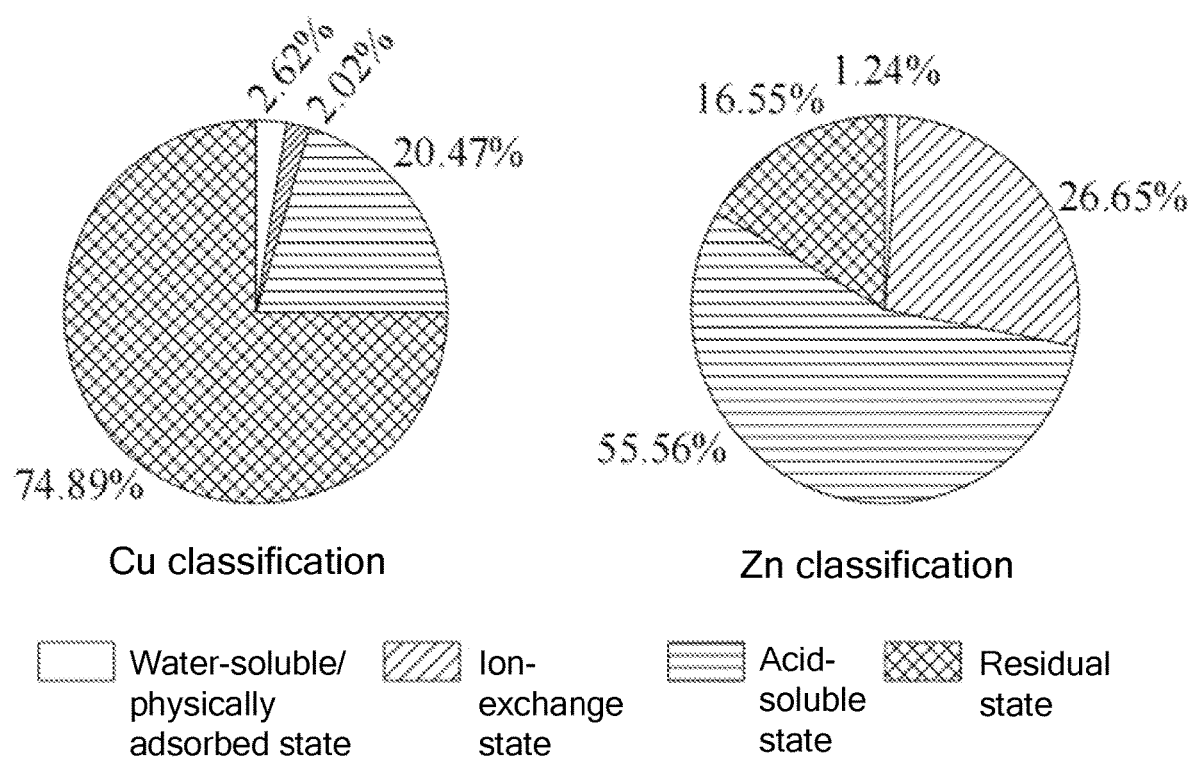
FIG. 6 shows proportions of forms of copper and zinc adsorbed by the cress vermicompost in the compound polluted water body.

After drying, the cress vermicompost adsorbed with copper and zinc was extracted step by step with water, 0.5 mol $L^{-1}$ $MgCl_2$, 1.0 mol $L^{-1}$ NaOAc and mixed acid (9 ml of 36% HCl and 3 ml of 70% $HNO_3$) to obtain copper and zinc in a water-soluble/physically bound state, an ion-exchange state, an acid-soluble state, and a residual state. The results showed that there were significant differences in the binding forms of copper and zinc in the cress vermicompost (FIG. 6). The adsorbed copper was mainly in an acid-soluble state and a residual state, accounting for 20.47% and 74.89% respectively. The adsorbed zinc was mainly in an ion-exchange state, an acid-soluble state and a residual state, accounting for 26.65%, 55.56%, and 16.55% respectively. This also showed that the cress vermicompost was more closely bound to copper.

The above described are preferred implementations of the present disclosure, and it should be noted that for those of ordinary skill in the art, various improvements and modifications may be made without departing from the principles of the present disclosure. These improvements and modifications should be regarded as falling within the protection scope of the present disclosure.

What is claimed is:

1. A preparation method of vermicompost made of aquatic plants, comprising: mixing aquatic plant residues and fresh cow dung according to a 1:1 weight ratio, and crushing the aquatic plant residues while stirring until even mixing to obtain a mixture; adding earthworms to the mixture of the aquatic plant residues and the cow dung, wherein the earthworms transform the mixture of the aquatic plant residues and the cow dung in a forest at 15-35° C., and moisture in the mixture is maintained at 65-75% in the process; and after 35-45 days, separating the earthworms and vermicompost, and drying the vermicompost to obtain the vermicompost made of aquatic plants; wherein the aquatic plant residues are lotus leaves or cress.

2. The preparation method of vermicompost made of aquatic plants according to claim 1, wherein the mixture of the aquatic plant residues and the cow dung and the earthworms have a weight ratio of 20:1.

3. The preparation method of vermicompost made of aquatic plants according to claim 1, wherein the vermicompost has a moisture content less than or equal to 30%.

4. The preparation method of vermicompost made of aquatic plants according to claim 1, wherein the aquatic plant residues are stirred and crushed with a shovel or forklift.

5. The preparation method of vermicompost made of aquatic plants according to claim 1, wherein the earthworm is *Eisenia foetida*.

6. Vermicompost made of aquatic plants prepared by the preparation method according to claim 1, wherein the vermicompost comprises aquatic plant residues and cow dung in a weight ratio of 1:1, and wherein the aquatic plant residues are lotus leaves or cress.

7. The vermicompost made of aquatic plants according to claim 6, wherein the mixture of the aquatic plant residues and the cow dung and the earthworms have a weight ratio of 20:1.

8. The vermicompost made of aquatic plants according to claim 6, wherein the vermicompost has a moisture content less than or equal to 30%.

9. The vermicompost made of aquatic plants according to claim 6, wherein the aquatic plant residues are stirred and crushed with a shovel or forklift.

10. The vermicompost made of aquatic plants according to claim 6, wherein the earthworm is *Eisenia foetida*.

11. A method for removing copper-zinc compound pollution from a water body, comprising putting the vermicompost made of aquatic plants according to claim 6 into a water body polluted by a copper-zinc compound.

12. The method according to claim 11, wherein the mixture of the aquatic plant residues and the cow dung and the earthworms have a weight ratio of 20:1.

13. The method according to claim 11, wherein the vermicompost has a moisture content less than or equal to 30%.

14. The method according to claim 11, wherein the aquatic plant residues are stirred and crushed with a shovel or forklift before putting the vermicompost made of aquatic plants according to claim 6 into a water body polluted by a copper-zinc compound.

15. The method according to claim 11, wherein the earthworm is *Eisenia foetida*.

16. The method according to claim 11, wherein the vermicompost made of aquatic plants has a dosage of 1.0-2.0 g $L^{-1}$.

17. The method according to claim 12, wherein the vermicompost made of aquatic plants has a dosage of 1.0-2.0 g $L^{-1}$.

* * * * *